(12) United States Patent
Liao

(10) Patent No.: US 12,359,782 B1
(45) Date of Patent: Jul. 15, 2025

(54) LED CANDLE WARMER LAMP

(71) Applicant: Xianhua Liao, Hunan (CN)

(72) Inventor: Xianhua Liao, Hunan (CN)

( * ) Notice: Subject to any disclaimer, the term of this patent is extended or adjusted under 35 U.S.C. 154(b) by 0 days.

(21) Appl. No.: 19/018,201

(22) Filed: Jan. 13, 2025

(30) Foreign Application Priority Data

Dec. 24, 2024 (CN) .......................... 202423223753.7

(51) Int. Cl.
| | | |
|---|---|---|
| *F21S 6/00* | (2006.01) | |
| *F21S 4/28* | (2016.01) | |
| *F21V 23/00* | (2015.01) | |
| *F21V 29/90* | (2015.01) | |
| *A61L 9/012* | (2006.01) | |
| *A61L 9/03* | (2006.01) | |
| *F21Y 105/18* | (2016.01) | |
| *F21Y 115/10* | (2016.01) | |

(52) U.S. Cl.
CPC ............... *F21S 6/002* (2013.01); *F21S 4/28* (2016.01); *F21V 23/002* (2013.01); *F21V 23/008* (2013.01); *F21V 29/90* (2015.01); *A61L 9/012* (2013.01); *A61L 9/03* (2013.01); *A61L 2209/12* (2013.01); *F21Y 2105/18* (2016.08); *F21Y 2115/10* (2016.08)

(58) Field of Classification Search
CPC ........... F21S 6/002; F21S 4/28; F21V 23/002; F21V 23/008; F21V 29/90; A61L 9/012; A61L 9/03; A61L 2209/12; F21Y 2105/18; F21Y 2115/10
See application file for complete search history.

(56) References Cited

U.S. PATENT DOCUMENTS

| | | | | |
|---|---|---|---|---|
| 11,421,850 | B1* | 8/2022 | Hsiao ....................... | F21S 10/00 |
| 11,727,791 | B2* | 8/2023 | Myoung ................... | A61L 9/03 |
| | | | | 340/12.29 |
| 12,253,254 | B1* | 3/2025 | Yi .......................... | F21V 35/003 |
| 2023/0102286 | A1* | 3/2023 | J N ....................... | F21V 23/0435 |
| | | | | 362/231 |
| 2023/0226240 | A1* | 7/2023 | Ma ........................ | H05B 1/0252 |
| | | | | 422/125 |
| 2023/0366527 | A1* | 11/2023 | He ......................... | F21V 23/001 |
| 2024/0066171 | A1* | 2/2024 | Yoo ............................ | A61L 9/03 |
| 2024/0161663 | A1* | 5/2024 | Knight .................... | G09F 13/36 |
| 2024/0173450 | A1* | 5/2024 | Gong ........................ | A61L 9/03 |

\* cited by examiner

*Primary Examiner* — Evan P Dzierzynski
(74) *Attorney, Agent, or Firm* — Daniel M. Cohn

(57) ABSTRACT

An LED candle warmer lamp includes a base and a light diffusing shell. The light diffusing shell is connected to the base. An LED light strip is disposed between the base and the light diffusing shell. The LED light strip includes LED lamp beads. A limiting hole allowing a power line to pass through is defined on the light diffusing shell. The power line is electrically connected to the LED light strip. An accommodating groove is defined on a top end of the base. A fixing rod is disposed adjacent to one side of the accommodating groove. A heating lamp disposed over the accommodating groove is connected to the fixing rod. When in use, a candle is placed in the accommodating groove, the heating lamp is turned on, and a switch is turned on to control a brightness and a color temperature of the LED lamp beads.

9 Claims, 4 Drawing Sheets

LED CANDLE WARMER LAMP

TECHNICAL FIELD

The present disclosure relates to a field of candle warmer lamp, and in particular to an LED candle warmer lamp.

BACKGROUND

Most conventional candle warmer lamps use candlelight as a light source, which not only limits an adjustment range of a brightness and a color temperature, but also causes safety hazards. Moreover, the candle is easily blown out by wind or extinguished due to vibration, affecting a use effect.

Therefore, how to provide a candle warmer lamp that is able to stably adjust a brightness and a color temperature thereof is an urgent problem to be solved.

SUMMARY

A main purpose of the present disclosure is to provide an LED candle warmer lamp to solve a technical problem that conventional candle warmer lamps are unable to adjust a brightness and a color temperature thereof.

To achieve the above purpose, the present disclosure provides the LED candle warmer lamp. The LED candle warmer lamp comprises a base and a light diffusing shell.

The light diffusing shell is disposed on a peripheral side of the base. An LED light strip is disposed between the base and the light diffusing shell. The LED light strip comprises LED lamp beads. An accommodating groove configured to accommodate a candle is defined on a top end of the base. A fixing rod is disposed adjacent to one side of the accommodating groove. A heating lamp is connected to a top end of the fixing rod. The heating lamp is disposed over the accommodating groove.

Optionally, a mounting groove is defined on the peripheral side of the base. The LED light strip is disposed in the mounting groove. The light diffusing shell comprises a first light diffusing layer, a second light diffusing layer, and a connecting layer. The connecting layer is mounted on a bottom portion of the base. The first light diffusing layer and the second light diffusing layer are disposed on the connecting layer. The second light diffusing layer is attached to the mounting groove. The first light diffusing layer is disposed outside the second light diffusing layer. A minimum distance between the first light diffusing layer and the second light diffusing layer is not less than 1 millimeter (mm).

Optionally, the LED candle warmer lamp further comprises a bottom plate, the bottom plate is attached to the bottom portion of the base, and the first light diffusing layer is fixed between the bottom plate and an edge of an upper end surface of the base.

Optionally, a line storage groove configured to accommodate a power line is defined on the bottom portion of the base, and a bottom end of the fixing rod extends into the line storage groove.

Optionally, a limiting hole is defined on first light diffusing layer. The power line connected to the LED light strip passes through the limiting hole. The second light diffusing layer defines a first wiring notch corresponding to the limiting hole. One side wall of the line storage groove defines a second wiring notch corresponding to the limiting hole.

Optionally, the LED candle warmer lamp further comprises a power controller configured to control the LED candle warmer lamp. The power line of the power controller sequentially passes through the limiting hole, the first wiring notch and the second wiring notch to be wound in the line storage groove.

Optionally, a lampshade is disposed on a peripheral side of the heating lamp, the lampshade is connected to the fixing rod, and the heating lamp is fixedly disposed in the lampshade.

Optionally, an opening of the lampshade directly faces the accommodating groove, and a maximum cross-sectional area of the lampshade is less than an area of a bottom surface of the accommodating groove.

Optionally, a spherical connecting portion is disposed on a joint of the fixing rod and the lampshade, and the spherical connecting portion is fixedly connected to the lampshade.

Optionally, a first wiring channel is defined inside the fixing rod. A second wiring channel communicated with the first wiring channel is defined inside the spherical connecting portion. After being wound in the line storage groove, the power line passes through the first wiring channel, the second wiring channel, and the lampshade to be connected to the heating lamp.

In the present disclosure, when the LED candle warmer lamp is in use, the candle is placed in the accommodating groove, the heating lamp is turned on, and a switch is turned on to control a brightness and a color temperature of the LED lamp beads disposed around the base. Light emitted by the LED lamp beads is diffused by the light diffusing shell (which is made of acrylic) to be uniform and soft. Different color temperatures of the LED lamp beads create different atmospheres and enhance an aesthetic of the LED candle warmer lamp when in use.

BRIEF DESCRIPTION OF DRAWINGS

One or more embodiments are exemplarily described by corresponding drawings, which do not constitute limitations on the embodiments. Elements with the same reference numerals in the drawings represent similar elements, and the figures in the drawings do not constitute proportional limitations unless otherwise stated.

REFERENCE NUMERALS IN THE DRAWINGS

1—base; 11—accommodating groove; 12—mounting groove; 13—line storage groove; 131—second wiring notch; 2—light defusing cover; 21—first light defusing layer; 211—limiting hole; 22—second light defusing layer; 221—first wiring notch; 3—bottom plate; 4—LED light strip; 41—LED lamp bead; 5—fixing rod; 51—first wiring channel; 6—heating lamp; 61—lampshade; 62—spherical connecting portion; 621—second wiring channel; 7—power controller.

DETAILED DESCRIPTION

In order to facilitate the understanding of the present disclosure, the present disclosure is described in detail below in conjunction with the accompanying drawings and specific embodiments. It should be noted that when an element is described as "fixed to" another element, it may be directly fixed on the other element, or there may be one or more medium elements therebetween. When an element is described as "connected to" another element, it may be directly connected to the other element, or there may be one or more medium elements therebetween. The terms "vertical", "horizontal", "left", "right", "inside", "outside", and similar expressions used in the specification are for illustrative purposes only. In the description of the present disclosure terms such as "first" and "second" are only used for the purpose of description, rather than being understood to indicate or imply relative importance or hint the number of indicated technical features. Thus, the feature limited by "first" and "second" can explicitly or impliedly include one or more features. In the description of the present disclosure, the meaning of "a plurality of" is two or more unless otherwise specified. The term "include" and any variant are intended to cover non-exclusive inclusion, which may exist or add one or more other features, integers, steps, operations, units, components, and/or combinations thereof.

In addition, unless otherwise regulated and defined, terms such as "installation", "bonded", and "connection" shall be understood in broad sense, and for example, may refer to fixed connection or detachable connection or integral connection; may refer to mechanical connection or electrical connection; and may refer to direct connection or indirect connection through an intermediate medium or inner communication of two elements. Unless otherwise defined, all technical and scientific terms used herein have the same meaning as commonly understood by those skilled in the art of the present disclosure. The terms used in the description of the present disclosure herein are only for the purpose of describing specific embodiments, and are not intended to limit the present disclosure. The term "and/or" used in the present disclosure includes any and all combinations of one or more of the associated listed items.

In addition, the technical features involved in different embodiments of the present disclosure described below can be combined with each other as long as they do not conflict with each other.

Figure 1:
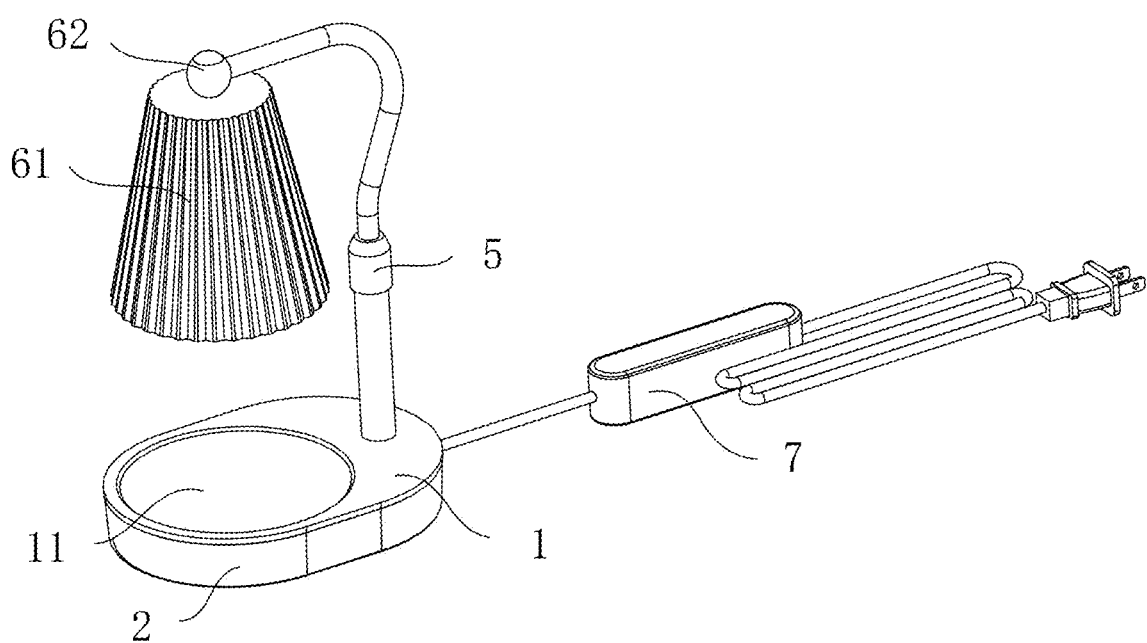
FIG. 1 is a perspective schematic diagram of an LED candle warmer lamp according to one embodiment of the present disclosure.
Figure 2:
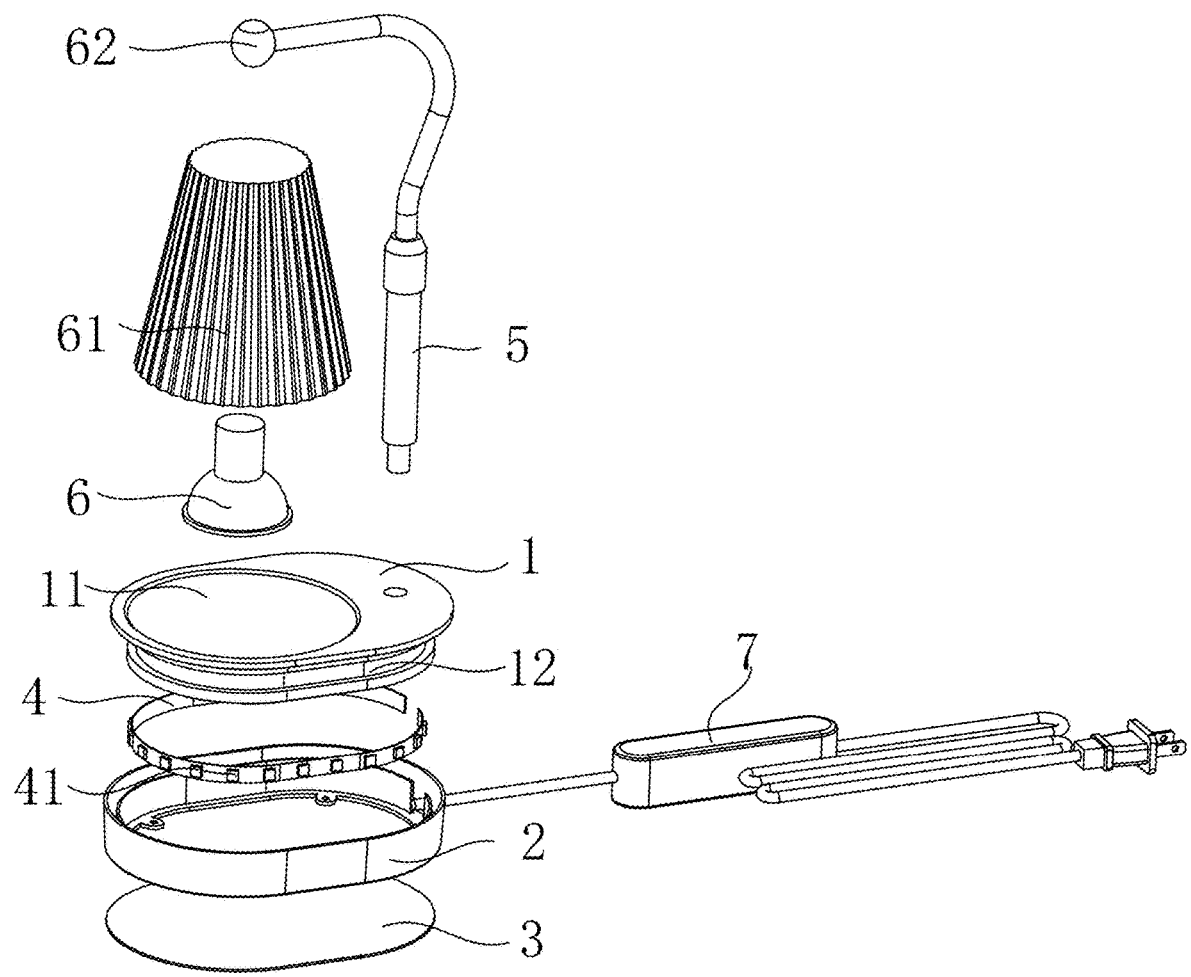
FIG. 2 is an exploded schematic diagram of the LED candle warmer lamp according to one embodiment of the present disclosure.
Figure 3:
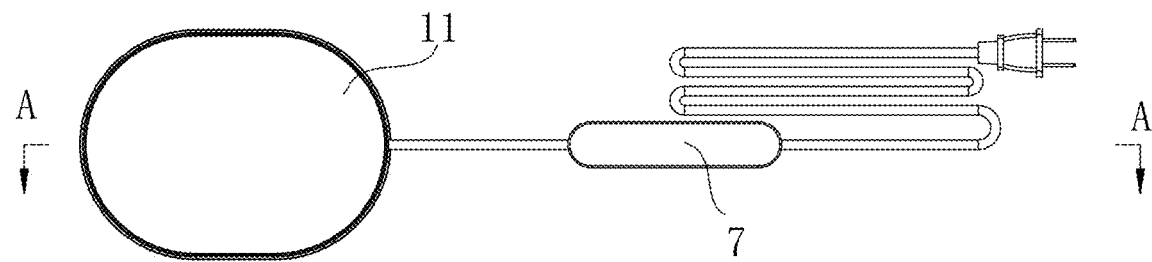
FIG. 3 is a top plan schematic diagram of the LED candle warmer lamp according to one embodiment of the present disclosure.
Figure 4:
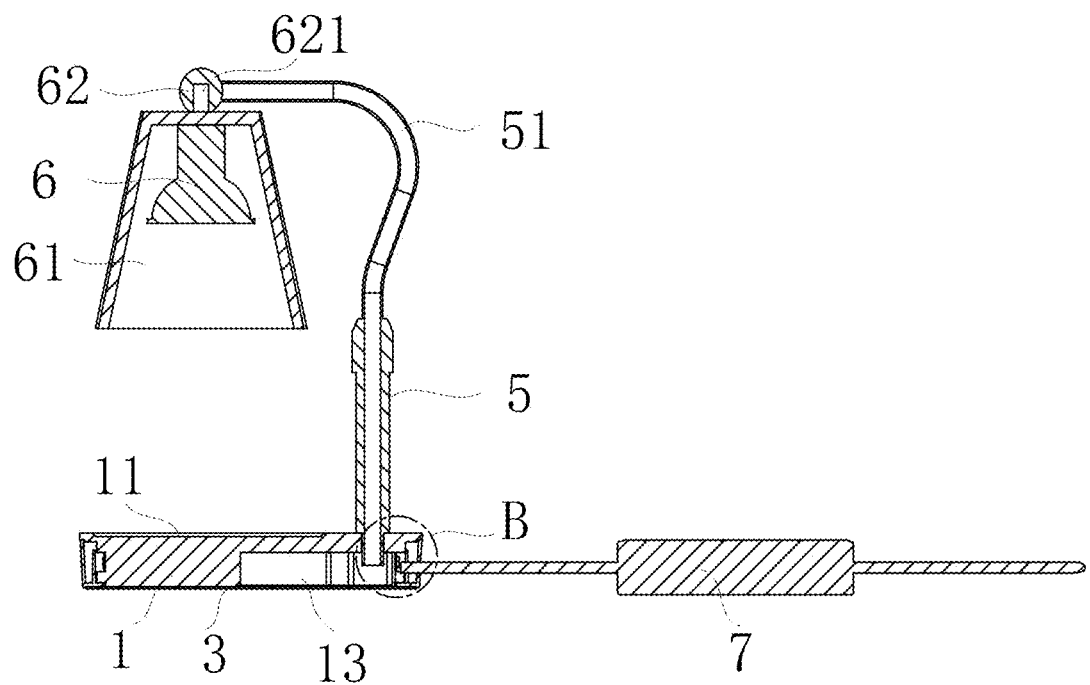
FIG. 4 is a cross-sectional schematic diagram of the LED candle warmer lamp taken along a line A-A shown in FIG. 3.
Figure 5:
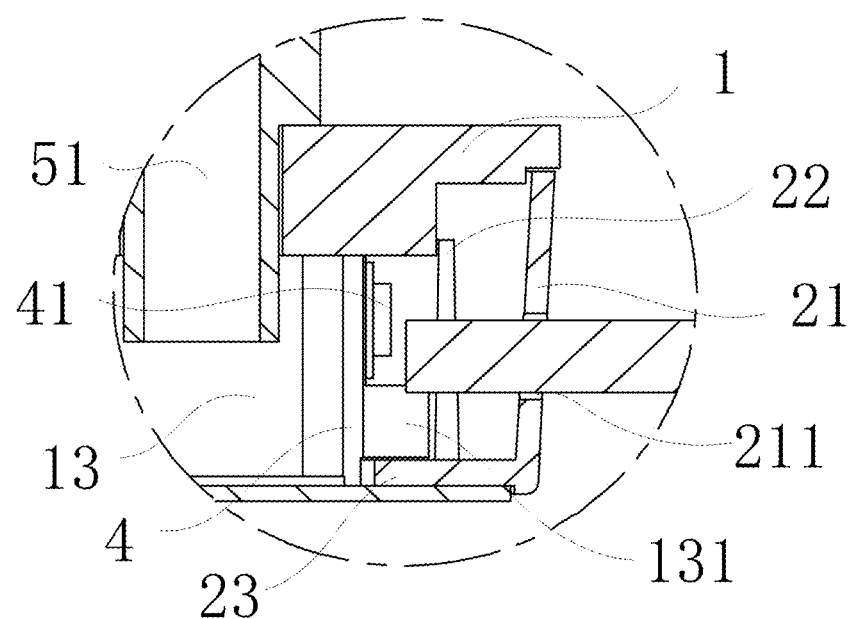
FIG. 5 is an enlarged schematic diagram of area B shown in FIG. 4.

As shown in FIGS. 1-5, the present disclosure provides an LED candle warmer lamp. The LED candle warmer lamp comprises a base 1 and a light diffusing shell 2. The light diffusing shell 2 is disposed on a peripheral side of the base 1. An LED light strip 4 is disposed between the base 1 and the light diffusing shell 2. The LED light strip 4 comprises LED lamp beads 41. An accommodating groove 11 configured to accommodate a candle is defined on a top end of the base 1. A fixing rod 5 is disposed adjacent to one side of the accommodating groove 11. A heating lamp 6 is connected to a top end of the fixing rod 5. The heating lamp 6 is disposed over the accommodating groove 11.

In the present disclosure, when the LED candle warmer lamp is in use, the candle is placed in the accommodating groove 11, the heating lamp 6 is turned on, and a switch is turned on to control a brightness and a color temperature of the LED lamp beads 41 disposed around the base 1. Light emitted by the LED lamp beads 41 is diffused by the light diffusing shell 2 (which is made of acrylic) to be more uniform and soft. Different color temperatures of the LED lamp beads 41 create different atmospheres and enhance an aesthetic of the LED candle warmer lamp when in use.

As shown in FIGS. 1-5, in the embodiment, a mounting groove 12 is defined on the peripheral side of the base 1. The LED light strip 4 is disposed in the mounting groove 12. The light diffusing shell 2 comprises a first light diffusing layer 21, a second light diffusing layer 22, and a connecting layer 23. The connecting layer 23 is mounted on a bottom portion of the base 1. The first light diffusing layer 21 and the second light diffusing layer 22 are disposed on the connecting layer 23. The second light diffusing layer 22 is attached to the mounting groove 12. The first light diffusing layer 21 is disposed outside the second light diffusing layer 22. A minimum distance between the first light diffusing layer 21 and the second light diffusing layer 22 is not less than 1 millimeter (mm). A configuration of a spacing between the first light diffusing layer 21 and the second light diffusing layer 22 optimizes a propagation path of the light and reduces reflection and refraction loss of the light transmitted from the light diffusing shell 2. Further, the configuration of the spacing helps to reduce glare or bright spots formed on a surface of the light diffusing shell 2 and improve an overall light quality.

As shown in FIGS. 1-5, in the embodiment, a line storage groove 13 configured to accommodate a power line is defined on the bottom portion of the base 1, and a bottom end of the fixing rod 5 extends into the line storage groove 13. The LED candle warmer lamp further comprises a bottom plate 3. The bottom plate 3 is attached to the bottom portion of the base 1. The first light diffusing layer 21 is fixed between the bottom plate 3 and an edge of an upper end surface of the base 1.

A limiting hole 211 is defined on first light diffusing layer 21. The power line connected to the LED light strip 4 passes through the limiting hole 211. The second light diffusing layer 22 defines a first wiring notch 221 corresponding to the limiting hole 211. One side wall of the line storage groove 13 defines a second wiring notch 131 corresponding to the limiting hole 211. The LED candle warmer lamp further comprises a power controller 7 configured to control the LED candle warmer lamp. The power line of the power controller 7 sequentially passes through the limiting hole 211, the first wiring notch 221 and the second wiring notch 131 to be wound in the line storage groove 13. Moreover, the power line is electrically connected to the heating lamp 6 through the bottom end of the fixing rod 5, which ensures that the power line of the power controller 7 being able to smoothly pass through the light diffusing shell 2 and be connected to the heating lamp 6. Specifically, the power controller 7 integrates functions of charging, controlling on and off of the LED light strip, switching a color of the LED lamp beads 41, switching a flashing mode of the LED lamp beads 41, and adjusting a color temperature of the LED lamp beads 41.

As shown in FIGS. 1-5, in the embodiment, a lampshade 61 is disposed on a peripheral side of the heating lamp 6, the lampshade 61 is connected to the fixing rod 5, and the heating lamp 6 is fixedly disposed in the lampshade 61. An opening of the lampshade 61 directly faces the accommodating groove 11, and a maximum cross-sectional area of the lampshade 61 is less than an area of a bottom surface of the accommodating groove 11, which prevents heat generated by the heating lamp 6 from being directly dissipated into a surrounding environment. Instead, the heat is directed more to the candle placed in the accommodating groove 11.

Further, a user is prevented from directly contacting a high-temperature portion of the heating lamp 6, thereby avoiding a risk of burns.

As shown in FIGS. 1-5, in the embodiment, a spherical connecting portion 62 is disposed on a joint of the fixing rod 5 and the lampshade 61, and the spherical connecting portion 62 is fixedly connected to the lampshade 61.

Optionally, a first wiring channel 51 is defined inside the fixing rod 5. A second wiring channel 621 communicated with the first wiring channel 51 is defined inside the spherical connecting portion 62. After being wound in the line storage groove 13, the power line passes through the first wiring channel 51, the second wiring channel 621, and the lampshade 61 to be connected to the heating lamp 6. The spherical connecting portion 62 serves as a turning point of the power line, so that the power line is smoothly extended from an interior of the fixing rod 5 to an interior of the lampshade 61, thereby avoiding exposure and friction of the power line at the joint.

The above embodiments are only used to illustrate the technical solutions of the present disclosure, rather than to limit the present disclosure. Under the concept of the present disclosure, the technical features in the above embodiments or different embodiments may be combined, the steps may be implemented in any order, and there are many other changes in different aspects of the present disclosure as described above, which are not provided in detail for the sake of simplicity. Although the present disclosure is described in detail with reference to the embodiments, those skilled in the art should understand that the technical solutions described in the embodiments may modified, or some of the technical features may be replaced by equivalents. These modifications or replacements do not deviate the essence of the corresponding technical solutions from the scope of the technical solutions of the embodiments of the present disclosure.

What is claimed is:

1. An LED candle warmer lamp, comprising:
a base; and
a light diffusing shell;
wherein the light diffusing shell is disposed on a peripheral side of the base, an LED light strip is disposed between the base and the light diffusing shell, the LED light strip comprises LED lamp beads, an accommodating groove configured to accommodate a candle is defined on a top end of the base, a fixing rod is disposed adjacent to one side of the accommodating groove, a heating lamp is connected to a top end of the fixing rod, and the heating lamp is disposed over the accommodating groove;
wherein a mounting groove is defined on the peripheral side of the base, the LED light strip is disposed in the mounting groove, the light diffusing shell comprises a first light diffusing layer, a second light diffusing layer, and a connecting layer, the connecting layer is mounted on a bottom portion of the base, the first light diffusing layer and the second light diffusing layer are disposed on the connecting layer, the second light diffusing layer is attached to the mounting groove, the first light diffusing layer is disposed outside the second light diffusing layer, and a minimum distance between the first light diffusing layer and the second light diffusing layer is not less than 1 millimeter (mm).

2. The LED candle warmer lamp according to claim 1, wherein the LED candle warmer lamp further comprises a bottom plate, the bottom plate is attached to the bottom portion of the base, and the first light diffusing layer is fixed between the bottom plate and an edge of an upper end surface of the base.

3. The LED candle warmer lamp according to claim 2, wherein a line storage groove configured to accommodate a power line is defined on the bottom portion of the base, and a bottom end of the fixing rod extends into the line storage groove.

4. The LED candle warmer lamp according to claim 3, wherein a limiting hole is defined on first light diffusing layer, the power line connected to the LED light strip passes through the limiting hole, the second light diffusing layer defines a first wiring notch corresponding to the limiting hole, and one side wall of the line storage groove defines a second wiring notch corresponding to the limiting hole.

5. The LED candle warmer lamp according to claim 4, wherein the LED candle warmer lamp further comprises a power controller configured to control the LED candle warmer lamp, and the power line of the power controller sequentially passes through the limiting hole, the first wiring notch and the second wiring notch to be wound in the line storage groove.

6. The LED candle warmer lamp according to claim 5, wherein a lampshade is disposed on a peripheral side of the heating lamp, the lampshade is connected to the fixing rod, and the heating lamp is fixedly disposed in the lampshade.

7. The LED candle warmer lamp according to claim 6, wherein an opening of the lampshade directly faces the accommodating groove, and a maximum cross-sectional area of the lampshade is less than an area of a bottom surface of the accommodating groove.

8. The LED candle warmer lamp according to claim 7, wherein a spherical connecting portion is disposed on a joint of the fixing rod and the lampshade, and the spherical connecting portion is fixedly connected to the lampshade.

9. The LED candle warmer lamp according to claim 8, wherein a first wiring channel is defined inside the fixing rod, and a second wiring channel communicated with the first wiring channel is defined inside the spherical connecting portion; wherein after being wound in the line storage groove, the power line passes through the first wiring channel, the second wiring channel, and the lampshade to be connected to the heating lamp.

* * * * *